United States Patent
Dereume et al.

(10) Patent No.: US 6,554,858 B2
(45) Date of Patent: *Apr. 29, 2003

(54) INTRALUMINAL ENDOPROSTHESIS FOR RAMIFYING THE DUCTS OF A HUMAN OR ANIMAL BODY AND METHOD OF MANUFACTURE THEREOF

(75) Inventors: Jean-Pierre Georges Emile Dereume, Brussels (BE); Noureddine Frid, Beersel (BE)

(73) Assignee: Corvita Europe, Brussels (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,591
(22) PCT Filed: Apr. 25, 1997
(86) PCT No.: PCT/BE97/00049
§ 371 (c)(1), (2), (4) Date: Oct. 20, 1998
(87) PCT Pub. No.: WO97/40779
PCT Pub. Date: Nov. 6, 1997

(65) Prior Publication Data
US 2001/0004707 A1 Jun. 21, 2001

(30) Foreign Application Priority Data
Apr. 25, 1996 (BE) ................................. 9600264

(51) Int. Cl.$^7$ ............................................. A61F 2/06
(52) U.S. Cl. ............... 623/1.35; 623/1.13; 623/901; 623/1.16
(58) Field of Search ............... 623/1, 11, 12, 623/1.16, 1.27, 1.35, 901, 1.13, 1.28, 1.29, 1.2; 606/194

(56) References Cited

U.S. PATENT DOCUMENTS

| | | | |
|---|---|---|---|
| 4,140,126 A | 2/1979 | Choudhury | 128/325 |
| 4,323,525 A | 4/1982 | Bornat | 264/24 |
| 4,475,972 A | 10/1984 | Wong | 156/167 |
| 4,512,338 A | 4/1985 | Balko et al. | 128/1 R |
| 4,733,665 A | 3/1988 | Palmaz | 128/343 |
| 4,739,762 A | 4/1988 | Palmaz | 128/343 |
| 4,776,337 A | 10/1988 | Palmaz | 128/343 |
| 4,878,908 A | 11/1989 | Martin et al. | 623/1 |
| 4,994,071 A | 2/1991 | MacGregor | 606/194 |

(List continued on next page.)

FOREIGN PATENT DOCUMENTS

| | | |
|---|---|---|
| EP | 0 009 941 | 8/1980 |
| EP | 0 183 372 | 6/1986 |
| EP | 0 461 791 A1 | 12/1991 |
| EP | 0 539 237 A1 | 4/1993 |

(List continued on next page.)

OTHER PUBLICATIONS

"Transfemoral intraluminal graft implantation for abdominal aortic aneurysms"by Parodi, Annals of Vascular Surgery, vol. 5, No. 6, 1991.

Primary Examiner—Bruce Snow
Assistant Examiner—Brian E Pellegrino

(57) ABSTRACT

Intraluminal prosthesis comprising a tubular trunk element (1), which is radially expandable and compressible and which axially has a cavity (2) open at its two ends and divided into several axial channels (7, 8), and at least one branch element (13) which is radially expandable and compressible and which axially has a cavity open at its two ends, being, in its compression position, independent of the trunk element and having, in the expansion position, one end within one of the said axial channels and another end outside the trunk element.

20 Claims, 5 Drawing Sheets

U.S. PATENT DOCUMENTS

| | | | |
|---|---|---|---|
| 5,019,090 A | 5/1991 | Pinchuk | 606/194 |
| 5,061,275 A | 10/1991 | Wallsten et al. | 623/1 |
| 5,092,877 A | 3/1992 | Pinchuk | 623/1 |
| 5,171,262 A | 12/1992 | MacGregor | 623/1 |
| 5,195,984 A | 3/1993 | Schatz | 606/195 |
| 5,507,769 A | 4/1996 | Marin et al. | 606/198 |
| 5,632,772 A * | 5/1997 | Alcime et al. | 623/1 |
| 5,639,278 A * | 6/1997 | Dereume et al. | 623/1 |
| 5,824,040 A * | 10/1998 | Cox et al. | 623/1 |
| 5,843,160 A * | 12/1998 | Rhodes | 623/1 |
| 5,906,641 A * | 5/1999 | Thompson et al. | 623/1.15 |

FOREIGN PATENT DOCUMENTS

| | | |
|---|---|---|
| EP | 0 551 179 A1 | 7/1993 |
| EP | 0 556 850 A1 | 8/1993 |
| EP | 0 603 959 A1 | 6/1994 |
| EP | 0 621 015 A1 | 10/1994 |
| EP | 0 686 379 A2 | 12/1995 |
| FR | 2 678 508 | 1/1993 |
| GB | 1205743 | 9/1970 |
| WO | WO83/03752 | 11/1983 |
| WO | WO92/06734 | 4/1992 |
| WO | WO94/01056 | 1/1994 |
| WO | WO96/07371 | 3/1996 |

OTHER PUBLICATIONS

"Abdominal Aortic Aneurysms:Preliminary Technical and Clinical Results with Transfemoral Placement of Endovascular self–expanding stent grafts", By Blum et al, in Interventional Radiology, Jan. 1996, vol. 198, No. 1.

"Bifurcated Endovascular graft insertion for abdominal aortic aneurysm" by Chuter, in Vascular and Endovascular Surgical Techniques, W.D. Sanders Co., 1994.

* cited by examiner

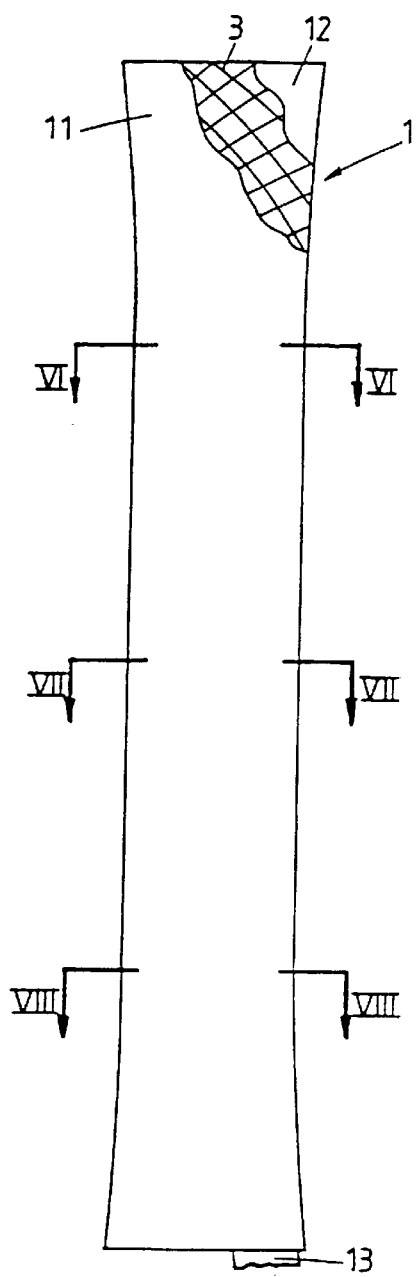
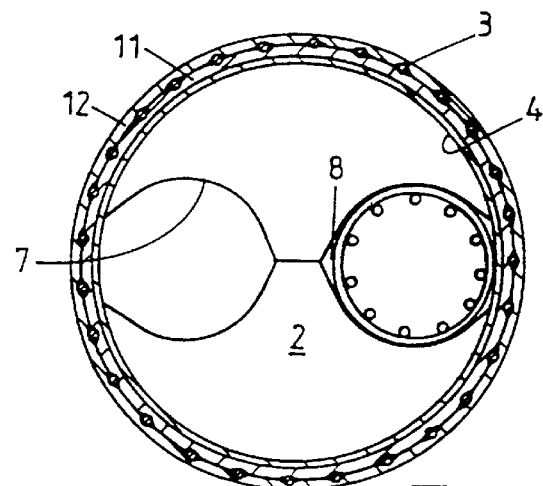
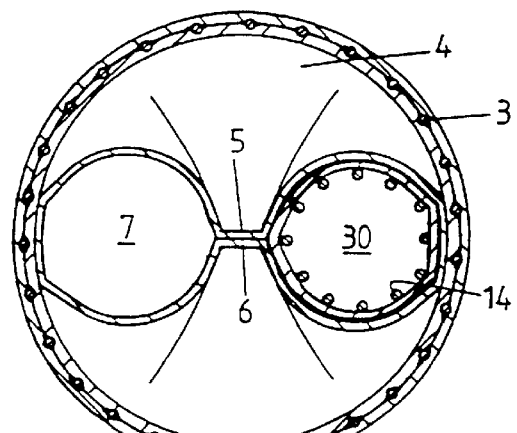
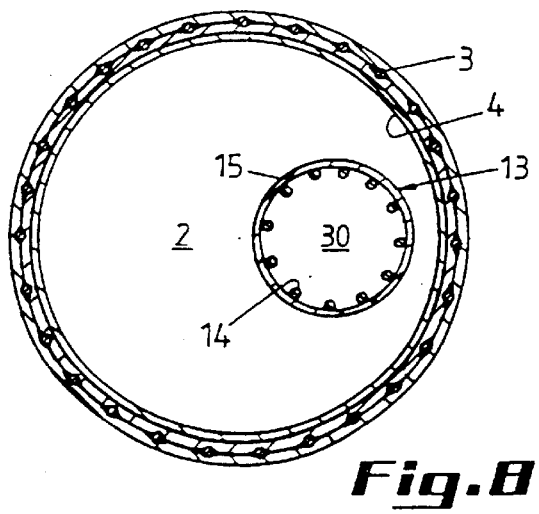
Fig.5
Fig.6
Fig.7
Fig.8

INTRALUMINAL ENDOPROSTHESIS FOR RAMIFYING THE DUCTS OF A HUMAN OR ANIMAL BODY AND METHOD OF MANUFACTURE THEREOF

BACKGROUND OF THE INVENTION

1. Field of the Invention

The present invention concerns an intraluminal prosthesis for a ramification of vessels in the human or animal body. It also relates to a tubular trunk element to be used in such an intraluminal prosthesis and to the method for producing such a tubular trunk element.

2. State of the Art

It has long been attempted to remedy various forms of deterioration which become manifest in the walls of the vessels in the human or animal body, such as the blood vessels, the canals of the gastrointestinal system, the urinary canals, and others. An example of a very common form of deterioration of the type in question involves aneurysms of the blood vessels, in particular aneurysms which affect the infrarenal segments of the abdominal aorta. There, the aorta undergoes dilation, leading to the risk of rupture of the vessel wall and the death of the patient.

Intraluminal prostheses have been used in an attempt to support the defective vessel walls. Various types of intraluminal prostheses with this purpose are described in the literature, and in particular in Patents U.S. Pat No. 4,140,126 and 4,512,332, and in International Patent Applications PCT WO 94/01056 and WO 96/07371. Mention may also be made of PARODI J. C. et al, Transfemoral Intraluminal Graft Implantation for Abdominal Aortic Aneurysms, Annals of Vascular Surgery, Vol. 5, No. 6, 1991, p. 491–499.

These documents describe fixing an intraluminal prosthesis to the distal and proximal necks of the aneurysm, for example an abdominal aortic aneurysm, that is to say to those parts which are the least affected at the onset of the condition. The proximal neck is situated below the renal arteries, and the distal neck is situated just above the aorto-iliac bifurcation. However, no solution is proposed when the aneurysm extends into the branches of this ramification. During the exponential growth of the aneurysm, the necks do in fact also become the site of dilation, particularly the distal neck, and then the iliac arteries. In cases such as this, which are very common, the solutions proposed hereinabove are inadequate.

Attempts have therefore been made to provide intraluminal prostheses for ramifications.

For example, bifurcated intraluminal prostheses are known which have the general appearance of trousers, having, at the three ends, a fastening stent element to be fixed to the proximal neck of the aneurysm and in healthy segments of the iliac arteries (see EP-A-0461791 and EP-A-0539237; T. CHUTER, Bifurcated endovascular graft insertion for abdominal aortic aneurysm, in "Vascular and Endovascular Surgical Techniques", 3rd ed., Ed. RM Greenhalg Publication WD Saunders Company, 1994, p. 92–99). These intraluminal prostheses have the disadvantage of being difficult to place, after aortic release, for introducing each of the legs of the intraluminal prosthesis into their iliac artery. It is generally necessary to use devices for recovery of a femoral cruciate catheter, which demands a high degree of skill on the part of the surgeon.

Other known bifurcated intraluminal prostheses comprise an aortic segment which is continued via an iliac segment. A branch stump measuring 5 mm in diameter protrudes laterally and has to be placed opposite the mouth of the iliac artery not yet provided with its intraluminal prosthesis. It is then necessary to introduce, via this iliac artery, an additional tube which is to be inserted into this small tubular stump. This necessitates a precise positioning of the latter, which is attempted by arranging radiopaque markers on the intraluminal prosthesis (see BLUM U. et al, Abdominal Aortic Aneurysms . . . , International Radiology, Vol. 198, Jan. 1, 1996, p. 25–31). Just as in the above solution, the surgeon needs to be highly skilful to introduce the additional tube into the tubular stump intended for it, and he must have great expertise in the use of intraluminal catheters.

All these embodiments, whether bifurcated with one trunk and two complete legs, or with one trunk, one complete leg and one leg to be inserted in situ into a stump, have the disadvantage of a complicated design. In addition, they are generally supported in a rigid manner by fastening stent elements, uniquely at the proximal neck and in the iliac arteries, hence the danger of too pronounced a bend in one of the two legs at the site of the bifurcation.

In attempting to overcome this latter disadvantage, expandable and retractable stents have been provided which can support a covering, itself also expandable, along the entire length of the bifurcated intraluminal prosthesis. A model of a bifurcated stent, expandable by balloon, has been provided in U.S. Pat. No. 4,994,071, for example. It is clear, however, that the production of a bifurcated intraluminal prosthesis equipped with a complete bifurcated stent is complex and costly. Its introduction into the patient's body is certainly not easy either.

Finally, intraluminal prostheses are known which are formed by two tubular elements which are to be introduced simultaneously into the aneurysm, the first via one iliac artery, the second via the other iliac artery. The ends of these tubular elements, when they have reached the proximal neck of the aneurysm, are dilated radially in order to be fastened thereto simultaneously, whilst the opposite end of each of these elements is fastened in a similar manner in its corresponding iliac artery. According to one embodiment, a metal stent is dilated in the neck, prior to these operations, so as to receive the two dilatable ends of the aforementioned tubular elements (see EP-A-0551179).

These embodiments have the major disadvantage of not guaranteeing a perfect sealing of the two proximal ends of the tubular elements inside the proximal neck of the aneurysm. This inevitably results in leaks at the periphery of the tubular elements, penetration of blood into the aneurysm and the reestablishment, which is to be avoided, of the blood pressure at this site.

SUMMARY OF THE INVENTION

The object of the present invention is to overcome the problems faced and to provide an intraluminal prosthesis for a ramification of vessels in the human or animal body which is applicable to the majority of the anatomical conditions and which is easy to position without having special experience of catheterization. After it has been put into place, this intraluminal prosthesis cannot present any phenomenon of leakage of blood into the cavity of the aneurysm. Moreover, this intraluminal prosthesis will advantageously be very easy to produce and to store.

This problem is resolved by means of an intraluminal prosthesis for a ramification of vessels in the human or animal body, comprising:

a tubular trunk element which is radially expandable and compressible and which is to be applied in the expansion position in a principal vessel of the said ramification, this tubular trunk element axially having two ends and a cavity which is open at these two ends, and at least one tubular branch element which is radially expandable and compressible and which axially has two ends and a cavity open at these two ends, each branch element being, in its compression position, independent of the tubular trunk element, this intraluminal prosthesis being characterized in that the cavity of the trunk element is divided into several axial channels over at least part of its length, and in that each branch element has an end which is to be applied, in the expansion position, within one of the said axial channels of the tubular trunk element, and another end situated outside the tubular trunk element, within a secondary vessel of the said ramification.

This intraluminal prosthesis has the advantage of being made up of independent elements, that is to say elements which are to be introduced successively into the body, and which have an external shape similar to the tubular intraluminal prostheses which are known at present. The trunk element is released between the distal and proximal necks of the aneurysm in a conventional manner, like a non-bifurcated intraluminal prosthesis. Each branch element is then introduced via one end inside the trunk element, while remaining at the other end in its corresponding iliac artery. The division of the internal cavity of the tubular trunk element into two axial channels has the effect of artificially displacing the branch a certain distance from the deteriorated branch. The application of a tubular branch element into each axial channel has the effect of preventing any phenomenon of leakage of blood into the aneurysm.

The axial channels are advantageously provided uniquely on a central part of the axial cavity of the tubular trunk element. As will be seen hereinafter, this embodiment facilitates the introduction of the guide and its introducer, then of its branch element, inside the trunk element which is already in place. Furthermore, the bifurcation obtained by two branch elements, fastened at the centre of the trunk element, softens the curvature of the branch elements, which promotes the flow of the body fluids.

According to one advantageous embodiment, the tubular trunk element comprises, between its ends, a sleeve made of flexible, biocompatible material, which is impermeable to the body fluids passing through the said ramification and which forms the said cavity and its channels, and, at least at each end of the trunk element, a tubular stent element which is radially expandable and compressible and to which the sleeve is fixed. According to an improved embodiment of the invention, the tubular trunk element comprises, between its ends, a sleeve made of flexible, biocompatible material, which is impermeable to the body fluids passing through the said ramification and which forms the said cavity and its channels, and a tubular stent, which is radially expandable and compressible, which surrounds the sleeve and on which the latter is fixed at least at the ends of the tubular trunk element. There is therefore no need to envisage a bifurcated stent. It suffices to use tubular, non-bifurcated stents which are easy to make and which have long been known in the art. Such stents are, for example, self-expandable, or expandable by balloon, and examples which may be cited by way of reference are U.S. Pat. Nos. 4,733,655, 4,739,762, 4,776,337, 5,019,090, 5,061,275, 5,092,877, 5,171,262, 5,195,984, EP-A-0183372, EP-A-0556850, EP-A-0621015, GB-1205743, WO-83/03752, WO92/06734.

The sleeve can be made of any known biocompatible material which has, for example, already been used in the production of grafts or coverings for intraluminal prosthesis stents. Particular mention may be made of a material produced, for example, as described in U.S. Pat. Nos. 4,475,272, 4,323,525 or EP-A-0603959. This biologically inert material can be Dacron, Teflon, polyurethane, polycarbonate fibres, or similar materials.

Advantageously, the expandable tubular stent will, in the expansion position, have at least one end which widens outwards. It will preferably have a complete internal and/or external covering.

Each branch element is made in the form of an intraluminal prosthesis known per se and suitable for placing inside a secondary vessel of a ramification, for example an iliac artery.

According to one embodiment of the invention, each tubular branch element comprises, between its ends, a sheath made of a flexible, biocompatible material, which is impermeable to the body fluids passing through the said ramification and which forms its abovementioned cavity, and, at least at each end of the tubular branch element, a tubular stent element which is radially expandable and compressible and on which the sheath is fixed.

According to an advantageous embodiment of the invention, each tubular branch element comprises, between its ends, a tubular stent which is radially expandable and compressible and which has an internal and/or external covering made of a biocompatible material which is impermeable to the body fluids. In this case, as may be observed, the intraluminal prosthesis can be supported along its entire length by several tubular stents, one stent for the trunk element and one stent for each branch element, none of these stents being bifurcated.

The present invention also concerns a tubular trunk element to be used in an intraluminal prosthesis for a ramification of vessels in the human or animal body, this tubular trunk element being radially expandable and compressible and, in the expansion position, being applied in a principal vessel of the said ramification, the tubular trunk element axially having two ends and a cavity which is open at these two ends and which is divided into several axial channels over at least part of its length.

The invention also relates to methods for producing the tubular trunk element according to the invention which is to be used in an intraluminal prosthesis for a ramification of vessels in the human or animal body.

Forms or embodiments of the invention are indicated in the claims which follow.

Other details and features of the invention will be evident from the description which is given hereinafter by way of non-limiting example and with reference to the attached drawings.

BRIEF DESCRIPTION OF THE DRAWINGS

FIG. 5 represents a side elevation, partially cut away, of an alternative embodiment of the tubular trunk element according to the invention.

FIGS. 6 to 8 represent sectional views, on an enlarged scale, along the lines VI—VI, VII—VII and VIII—VIII in FIG. 5.

In the different drawings, identical or similar elements are designated by the same reference labels.

Figure 1:
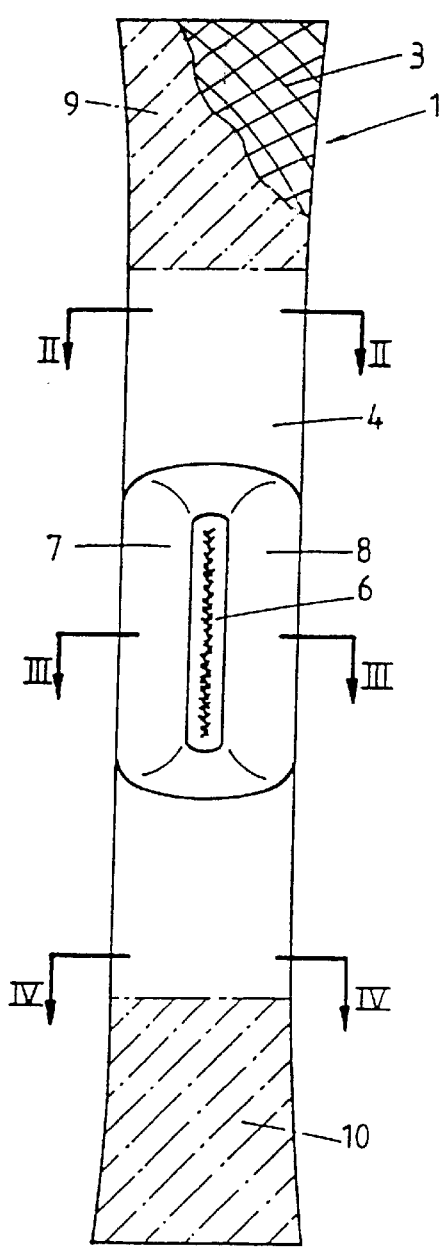
FIG. 1 represents a side elevation, partially cut way, of a tubular trunk element according to the invention, to be used in an intraluminal prosthesis according to the invention.
Figure 2:
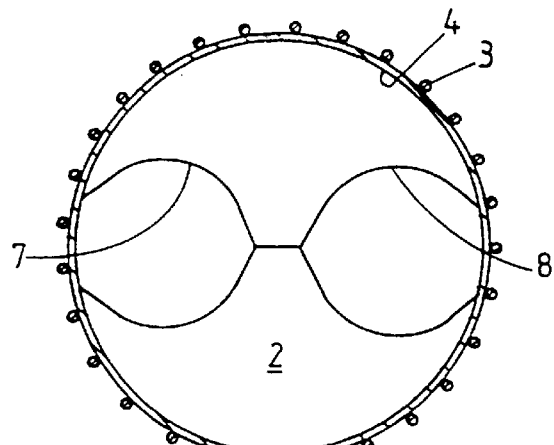
FIGS. 2 to 4 represent sectional views, on an enlarged scale, along the lines II—II, III—III and IV—IV in FIG. 1.
Figure 3:
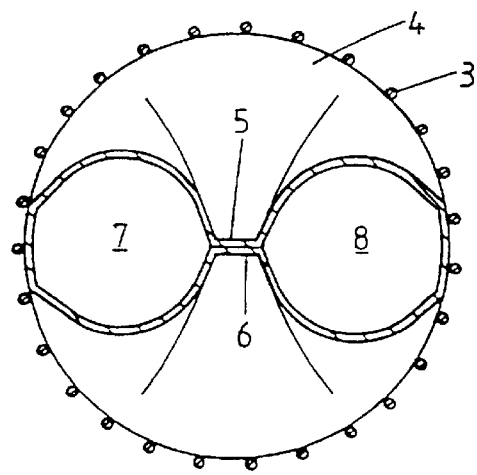
Figure 4:
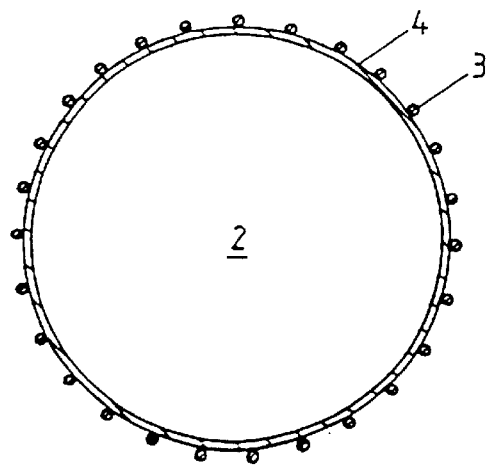

It should moreover be noted that, in FIGS. 2 to 4 and 6 to 8, the wires of the stents are represented in cross-section, and not in section like the other elements, in order to make the drawings easier to read. In these views, the proportions between the different elements are not necessarily true. For example, the thickness of the layers has been increased for better understanding of the drawing.

DETAILED DESCRIPTION OF THE PREFERRED EMBODIMENTS

FIGS. 1 to 4 represent an embodiment of a tubular trunk element, designated by the general reference 1, of an intraluminal prosthesis for a ramification according to the invention.

This tubular trunk element is radially expandable and compressible and is represented in the expansion position. It axially has two ends and a cavity 2 which is open at these two ends.

In the example illustrated, the tubular trunk element 1 comprises a tubular stent 3, known per se, in this case formed by a self-expandable tubular lattice, for example based on individual metal wires, and a sleeve 4 made of a biocompatible and advantageously flexible material, which is impermeable to the body fluids passing through the said ramification.

The sleeve 4 has, in its central part, diametrally opposite parts 5 and 6 which are joined to each other, for example by stitching, sealing, heat-sealing, etc. The ends of the sleeve are fixed on the inner wall of the stent 3, for example by adhesive bonding.

The sleeve 4 delimits the internal cavity 2 of the tubular trunk element and, by virtue of its shape, it forms, inside the latter, an arrangement of two axial channels 7 and 8 which divide the cavity 2 into two parallel conduits which have a shape similar to vascular conduits and which are sealed off in a leaktight manner from one another and, in each case, from the aneurysm.

According to a particular embodiment of the invention, it is possible to imagine the stent 3 being replaced by stent elements 9 and 10 at the ends of the trunk element 1 for fastening the sleeve 4 in place (see FIG. 1 in dot-and-dash lines) The sleeve 4 is fixed at its ends to these stent elements, whereas it is not supported in its central part. Its narrowed form at this location into two axial channels 7 and 8 gives it improved resistance there to the radial internal pressure of the body fluid passing through the sleeve after the tubular trunk element 1 has been released.

It is also possible to imagine the stent or the stent elements being brought into the expansion position with the aid of an inflatable balloon, in a manner known per se.

The tubular lattice of the stent 3 illustrated can advantageously be formed by multiple wires. It will also preferably have, instead of a cylindrical shape, a shape with widened ends, so that it can be fixed more easily the necks of the aneurysm, as can be seen in FIGS. 10 to 14.

It is also possible to envisage an extension of the two channels 7 and 8 over a greater length of the trunk element 1.

In the embodiment illustrated in FIGS. 5 to 8, the stent 3 has an internal covering 11 and an external covering 12, for example made of a biocompatible material. Such a stent is well known in the art, for example in EP-A-0603959. The materials used for these coverings can be the same, and the sleeve 4 fixed to the inside of this stent is advantageously also itself made of this material.

This embodiment permits excellent adhesion of the sleeve 4 to two channels 7 and 8 inside the stent, as will be explained in greater detail hereinafter.

FIGS. 5 to 8 represent, in place, a radially retractable and expandable branch element 13 according to the invention. This tubular branch element 13 axially has two ends and a cavity 30 which is open at these ends. One of its ends is fixed in the channel 8. In the example illustrated, this branch element 13 comprises, as with a conventional intraluminal prosthesis, a tubular stent 14 known per se, here formed by a self-expandable tubular lattice, for example based on individual metal wires. This lattice here has an external covering 15 made of a biocompatible and advantageously flexible material, which is impermeable to the body fluids passing through the ramification.

As can be seen in FIG. 7, in its expansion position in the channel 8, the end of the branch element 13 bears against the inner wall of the channel 8 in a manner sealed against fluids. It can have a covering 15 made of a material identical to that of the covering or coverings of the stent 3 and identical to that of the sleeve 4. This branch element 13 can instead have an internal covering in place of the external covering 15 or it can include both coverings at the same time.

As is evident from FIG. 8, the branch element 13, outside the channel 8, floats quite freely in the cavity 2 of the tubular trunk element 1. It protrudes at one end of the latter (see FIG. 5). It is this end of the branch element 13 which will be situated inside an iliac artery, in the case of an abdominal arterial aneurysm.

In this position, the branch element 13 brings the iliac artery directly into communication with the upper part, in FIG. 5, of the trunk element 1, that is to say the part upstream of the channels 7 and 8. This communication is effected in a manner perfectly sealed off with respect to the channel 7, which does not yet contain a branch element (see FIG. 7), and to the cavity 2 in its lower part in FIG. 5 (see FIG. 8).

As will be seen in greater detail hereinafter, the intraluminal prosthesis according to the invention thus forms a non-anatomical bifurcation between separate intraluminal prosthesis elements which are introduced one inside the other in a sealed manner. That end of the trunk element of the intraluminal prosthesis via which the branch elements can be introduced is wide open and does not permit any incorrect manoeuvre for insertion of these into one of the channels 7 and 8.

It will be understood that other embodiments of the trunk element 1 may be envisaged without departing from the scope of the invention. For example, it is possible to imagine other ways of partitioning off two or more channels so that they are sealed off in relation to one another. A single flexible partition inside the stent (as shown diagrammatically in FIG. 10) might be suitable. An unsealed partitioning suffices if, when the branch elements are introduced, the sealing is then guaranteed by expansion of these elements.

The introduction of an intraluminal prosthesis according to the invention into an abdominal aortic aneurysm will now be described with reference to FIGS. 9 to 14. The aneurysm 17 in this abdominal aorta 18 is situated between the renal arteries 19, 20 and the iliac arteries 21, 22. The aneurysm 17 has two necks, namely the proximal neck 23 and the distal neck 24. The origins of the iliac arteries also each have an aneurysm 25 and 26.

Figure 9:
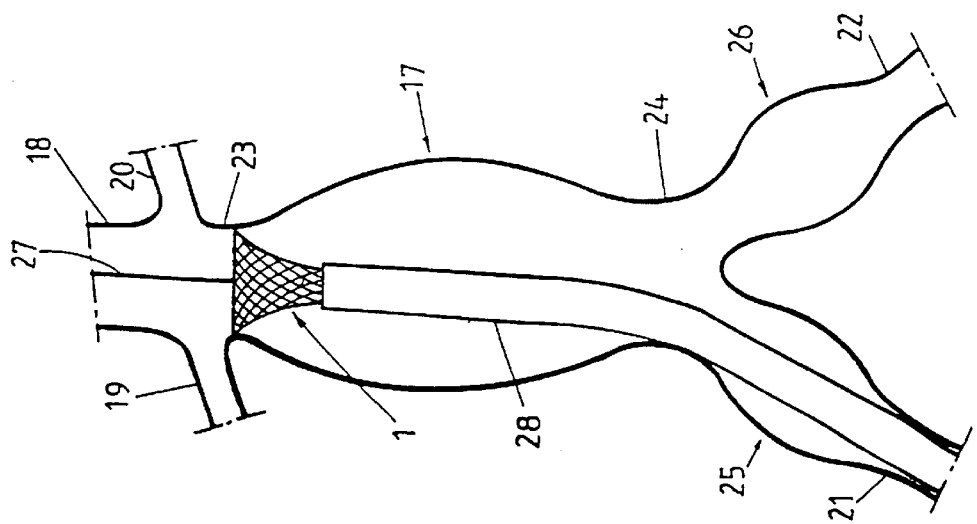

In a conventional manner, a guide 27, that is to say a long wire which will guide the sliding movement of an introducer 28 inside the iliac artery, then inside the aorta, is introduced from one of the iliac arteries 21 (see FIG. 9). When the introducer 28, thus guided, has reached the level of the proximal neck 23, the trunk element 1 according to the invention can be released, in the way a conventional intraluminal prosthesis is released (see, for example, U.S. Pat. No. 4,140,126), by simply withdrawing the introducer 28 and maintaining the trunk element 1 in place. The latter, in the example illustrated, then widens under the expansion action of the stent and, in this way, it bears on the proximal neck 23 in such a way as to seal off the aneurysm 17 with respect to the blood flow from the heart.

Figure 10:
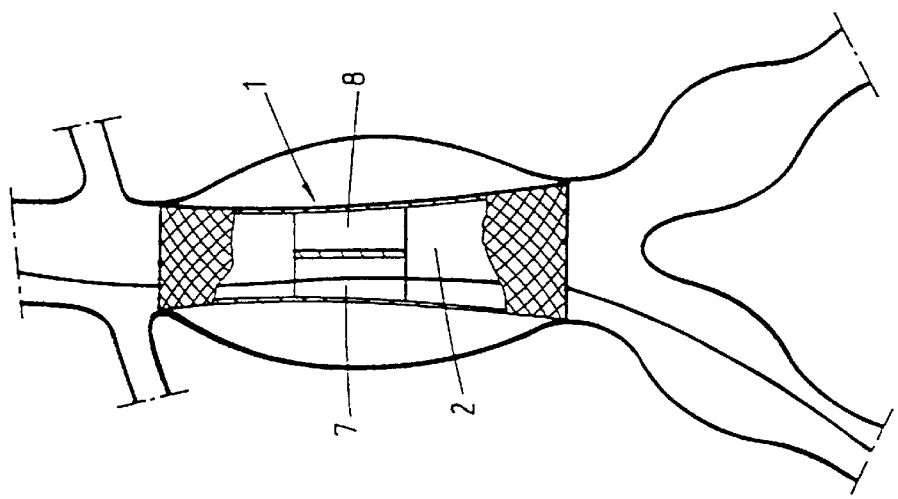

When, as is represented in FIG. 10, the introducer has been completely withdrawn, the trunk element 1, whose length has been calculated by the surgeon, is in place with each of its ends bearing on a neck of the aneurysm. The latter is now completely isolated from the blood flow passing through the abdominal aorta.

Figure 11:
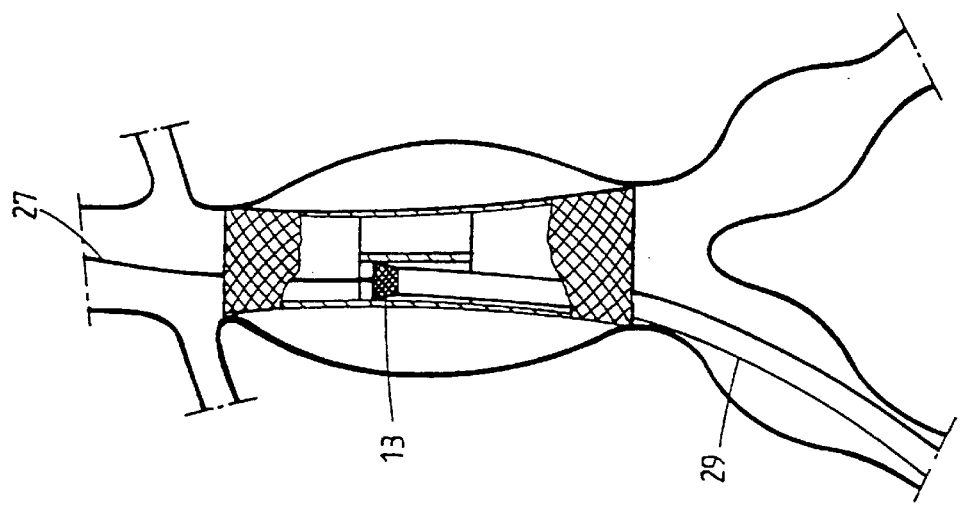
FIGS. 9 to 14 illustrate, in partially cut away views, a method of releasing an intraluminal prosthesis for a ramification according to the invention in the case of an abdominal aortic aneurysm.

A new introducer 29 is then introduced along the guide 27 which is still in place. This introducer penetrates without any problem into the cavity 2 of the trunk element 1. In a compressed position inside the introducer 29, a branch element 13 is situated there in a state totally independent of the trunk element 1. When, as represented in FIG. 11, the end of the introducer 29 easily reaches into one of the channels 7 of the trunk element 1, and then when the introducer 29 is withdrawn, maintaining the branch element 13 in place, the end of the latter changes to the expansion position. It then bears against the walls of the channel 7 through which the guide 27 passes.

Figure 12:
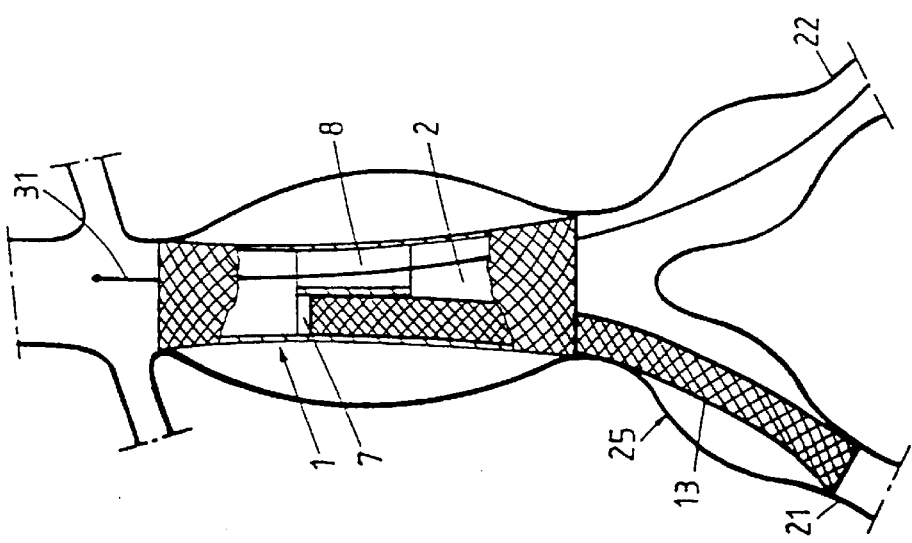

As is evident from FIG. 12, after complete withdrawal of the introducer 29, the other end of the branch element 13, the appropriate length of which has been calculated by the surgeon, bears against a healthy segment of the iliac artery, beyond the aneurysm 25.

A new guide 31 is then introduced via the other iliac artery 22. This guide penetrates inside the trunk element 1, without any problem, through the wide opening in its cavity 2. There, it can only pass through the channel 8, as the channel 7 is already closed off with respect to the lower part of the trunk element. Even if, in contrast to what is shown, the branch element 13 was placed between the iliac artery 21 and the channel 8, which is possible, the guide inserted via the iliac artery 22 could only pass through the unclosed channel, in this case the channel 7. This would in fact give a final configuration in which the branch elements are crossed, which would not pose any problem in terms of the blood flow.

Figure 14:
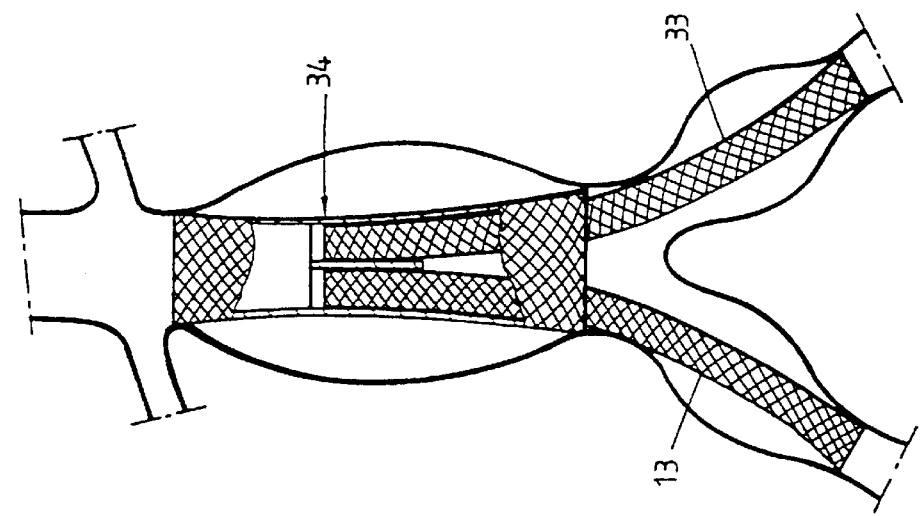
Figure 13:
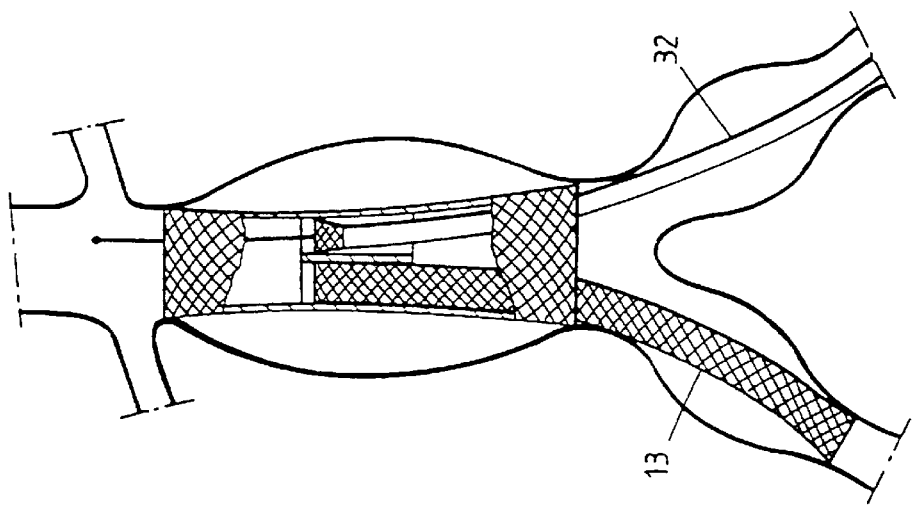

In the example illustrated in FIG. 13, a new introducer 32 is then slid along its guide 31, and a supplementary branch element 33 is then released, as represented in FIG. 14.

As can be seen in this figure, the anatomical branch has been elevated as far as the level indicated by the arrow 34. Starting from this level, the branch elements 13 and 33 exhibit a gentle curvature, with no danger of formation of a fold. The 3 aneurysms are now sealed off, without having required recourse to complicated manoeuvres using a catheter recovery device, or to a difficult alignment of intraluminal prosthesis sections opposite one another.

It is possible to imagine a somewhat different operation for positioning the intraluminal prosthesis. For example, after the step illustrated in FIG. 10, an inflatable balloon known per se can be introduced on the guide 27 for the purpose of closing the channel 7. The guide 31 is then introduced and finds itself forced to pass through the channel 8. The inflatable balloon is then withdrawn, while maintaining its guide in place. The two introducers 29 and 32 are then introduced simultaneously from the two iliac arteries and will each pass, without any problem, and simultaneously, into their appropriate channel.

Figure 15:
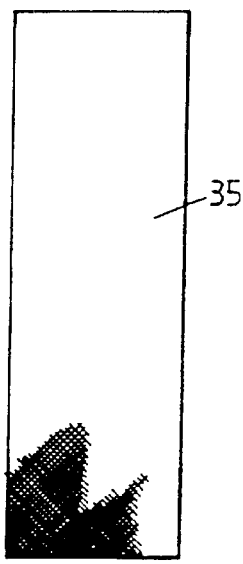
FIGS. 15 to 17 illustrate a method of producing the trunk element according to the invention.
Figure 16:
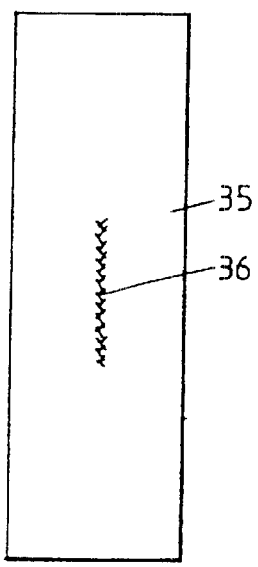

To produce an intraluminal prosthesis for a ramification of vessels in the human or animal body according to the invention, it is possible to envisage an internal sleeve made of a flexible and biocompatible material being joined to a stent or to stent elements. As has already been stated, these are well known in the art. To start with, the sleeve is produced in a cylindrical shape in any known manner, for example in accordance with the teaching of U.S. Pat. Nos. 4,323,525, 4,475,972, 4,878,908 and EP-A-0009941. The material used for producing such a sleeve can consist, although not necessarily, of a fibrous material which is advantageously elastic. It is possible to mention, as an example of very suitable fibres, polycarbonate fibres marketed by the company Corvita Corp. under the tradename Corethane®. The cylindrical sleeve 35 obtained, which is illustrated in FIG. 15, then undergoes a leaktight joining 36 of two diametrally opposite parts of its periphery in such a way as to form two axial channels over at least part of its length. This leaktight joining can be obtained, for example, by seams, stitches, heat sealing or cold sealing, or any other similar means.

The sleeve thus formed is then to be attached, by any suitable means, to the inner surface of the tubular stent or of the stent elements used.

Figure 17:
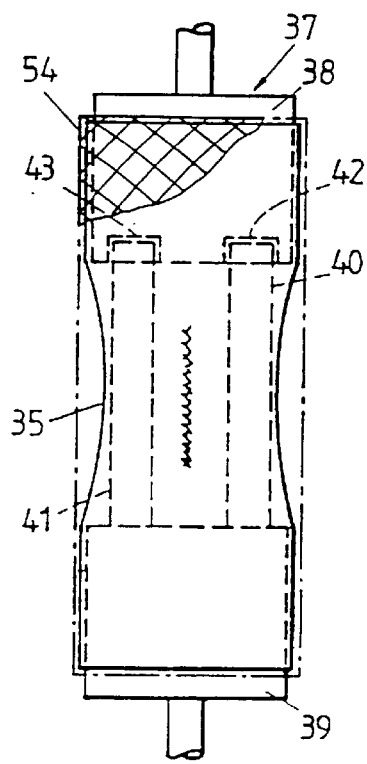

In this attachment step, it is possible to proceed as follows: a suitable mould is used, designated by reference 37 in FIG. 17. This mould 37 comprises two separable cylindrical ends 38 and 39. One of these ends, for example 39, is provided with two legs 40 and 41 which protrude parallel to one another and to the axis of the mould 37. After part of the sleeve 35 has been engaged on this end 39 of the mould by passing the legs 40 and 41 through the axial channels of the sleeve 35, the remaining part of the sleeve is engaged on the other end 38 of the mould 37. By closing the two mould parts 38 and 39 together, the two legs 40 and 41 of the part 39 penetrate into corresponding blind holes 42 and 43 provided in the part 38.

In this position, the sleeve 35 undergoes radial expansion. It is then possible to apply an adhesive to its surface and then to engage, over the sleeve, the stent 54 or the stent elements in the radially expanded position, at a diameter slightly greater than the diameter at rest. The stent then applies an inwardly directed pressure on the sleeve while the adhesive sets.

As adhesive, it is possible to envisage, for example, the material from which the sleeve is itself made. In the case of polycarbonate fibres, it is possible to prepare a solution of this material in a solvent, such as tetrahydrofuran. The stent is immersed in this solution before being engaged over the sleeve. After heating in a convection oven at 110° C. for a ½ hour, a trunk element according to the invention is obtained.

It is also possible, for example, to apply fibres wetted with polycarbonate on the sleeve 35 engaged on the mould 37, in accordance with the teaching given in EP-A-0603959.

When the stent immersed in the abovementioned adhesive solution is engaged over the mould, the very fine wetted fibres which have just been applied to the surface of the sleeve will act as a bridge between the film present on the inner surface of the stent and the sleeve. A polymer-polymer adhesion is obtained, the two polymers being of the same nature.

According to a preferred embodiment, the stent, before being engaged, has an internal covering made of polycarbonate fibres and, still more advantageously, at the same time an external covering, in the same way as the stents described in EP-A-0603959.

The adhesion energy level obtained between the sleeve and the stent can then be from 100 to 1000 $J/m^2$.

It should be understood that the present invention is not in any way limited to the forms and embodiments given hereinabove and that many modifications can be made thereto without departing from the scope of the invention indicated in the claims which follow.

What is claimed is:

1. An intraluminal prosthesis for a ramification of vessels which carry body fluids in the human or animal body, comprising:
    a) a tubular trunk element which is radially expandable and compressible and which is to be applied in the expansion position in a principal vessel of the ramification, said tubular trunk element axially having two ends, several axial channels, and a cavity which is open at its two ends, said trunk element comprised of:
        a sleeve made of a flexible, biocompatible material which is impermeable to the body fluids passing through the ramification, and which forms said cavity and said several axial channels, said sleeve having diametrically opposite portions which are joined to one another in a manner to form said axial channels over at least a portion of the length of said sleeve which are sealed against body fluids from each other, and
        a radially expandable and compressible tubular stent having a circular cross-section along its entire length, which surrounds said sleeve and on which said sleeve is fixed at least at said ends of said tubular trunk element; and
    b) at least one tubular branch element which is radially expandable and compressible and which axially has two ends and a cavity open at its two ends, each branch element being, in its compression position, independent of the tubular trunk element,
    wherein said branch element has an end which is to be applied, in the expansion position, within one of the said axial channels of said sleeve, and another end situated outside said tubular trunk element, within a secondary vessel of the ramification, and
    wherein said sleeve includes said axial channels only in an axially central part of said sleeve whereby said axial channels of said sleeve do not extend to either of said trunk component's two ends.

2. An intraluminal prosthesis according to claim 1, wherein:
    said tubular trunk element includes two axial channels.

3. An intraluminal prosthesis according to claim 1, wherein:
    said sleeve attached to said at least one tubular stent element forms an internal covering over at least part of said at least one tubular stent element.

4. An intraluminal prosthesis according to claim 1, wherein:
    each radially expandable and compressible tubular stent element includes an internal covering made of a biocompatible inert material which is impermeable to body fluids passing through the ramification.

5. An intraluminal prosthesis according to claim 1, wherein:
    said tubular trunk element comprises,
        (i) a radially expandable or compressible tubular stent between its ends which has a covering made of a biocompatible material which is impermeable to body fluids passing through the ramification, said covered tubular stent forming said cavity, and
        (ii) at least one flexible partition element fixed in said cavity in such a way as to divide said cavity over at least part of a length of said cavity into said several axial channels.

6. An intraluminal prosthesis according to claim 1, wherein:
    said tubular stent element has at least one of an internal covering and an external covering made of a biocompatible material which is impermeable to the body fluids.

7. An intraluminal prosthesis according to claim 1, wherein:
    said expandable tubular stent has, in the expansion position, at least one end which flares outward.

8. An intraluminal prosthesis according to claim 1, wherein:
    each said tubular branch element comprises,
        (i) a sheath made of a flexible, biocompatible material which is impermeable to the body fluids passing through the ramification and which forms its cavity and,
        (ii) a tubular stent element, at least at each end of the tubular branch element, which is radially expandable and compressible and on which the sheath is fixed.

9. An intraluminal prosthesis according to claim 1, wherein:
    each said tubular branch element comprises,
        (i) a tubular stent which is radially expandable and compressible, and
        (ii) at least one of an internal and an external covering made of a biocompatible material which is impermeable to the body fluids and coupled to said tubular stent.

10. An intraluminal prosthesis according to claim 1, wherein:
    said channels have a circular cross-section with a diameter which is approximately equal to the diameter of a secondary vessel of the ramification.

11. An intraluminal prosthesis according to claim 1, wherein:
    said sleeve attached on said tubular stent forms a direct internal covering over at least a portion of said stent.

12. An intraluminal prosthesis according to claim 1, wherein:
    said radially expandable and compressible tubular stent comprises an internal covering made of a biocompatible inert material which is impermeable to body fluids passing through the ramification and said sleeve is fixed to the stent at said internal covering.

13. An intraluminal prosthesis according to claim 1, wherein:
    said tubular stent has an external covering made of a biocompatible material which is impermeable to body fluids.

14. A trunk element for use as an intraluminal prosthesis for a ramification of vessels in the human or animal body, comprising:

a sleeve made of a flexible, biocompatible material which is impermeable to the body fluids passing through the ramification, said sleeve forming a cavity which is open at its two ends and at least two axial channels over at least a portion of said sleeve, said sleeve having diametrically opposite portions which are joined to one another in a manner to form said axial channels over at least a portion of the length of said sleeve which are sealed against body fluids from each other; and a radially expandable and compressible tubular stent having a circular cross-section along its entire length, which surrounds said sleeve and on which said sleeve is fixed at least at said ends of said tubular trunk element;

wherein said trunk element is radially expandable and compressible and, in the expansion position, capable of being implanted in a principal vessel of the ramification, and wherein said sleeve includes said axial channels only in an axially central part of said sleeve whereby said axial channels of said sleeve do not extend to either of said trunk component's two ends.

15. A method for producing a radially expandable and compressible tubular trunk element said trunk element having two ends, to be used in an intraluminal prosthesis for a ramification of vessels which carry body fluids in the human or animal body, comprising:

a) formation of a sleeve made of a flexible and biocompatible material, which is impermeable to the body fluids passing through the ramification;

b) joining in a leaktight manner two opposite peripheral parts of the sleeve, in such a way as to form two axial channels which do not extend to either of said ends of said trunk element; and c) attachment of the sleeve, over at least part of its length, to at least one radially expandable and compressible tubular stent element.

16. A method according to claim 15, wherein:

said joining is obtained by at least one of seams, stitches, heat sealing and cold sealing.

17. A method according to claim 15, wherein:

said attachment comprises radially expanding the sleeve at ends of the sleeve to a diameter greater than that of the at least one stent element, applying an adhesive to the periphery of the sleeve and engaging the at least one stent element on the sleeve coated with the adhesive.

18. A method according to claim 15, wherein:

said attachment comprises radially expanding the sleeve at ends of the sleeve to a diameter greater than that of the at least one element, immersing the at least one stent element in an adhesive and engaging the at least one stent element on the sleeve.

19. A method according to claim 15, wherein:

the at least one tubular stent element includes at least one of an internal covering and an external covering made of a flexible and biocompatible material.

20. A method according to claim 15, wherein:

said attachment comprises adhesion of the at least one tubular stent element to the sleeve by means of an adhesion of the flexible and biocompatible material.

* * * * *